United States Patent
Rygaard

[11] Patent Number: 5,993,468
[45] Date of Patent: Nov. 30, 1999

[54] METHOD AND ANASTOMOTIC INSTRUMENT FOR USE WHEN PERFORMING AN END-TO-SIDE ANASTOMOSIS

[75] Inventor: Jørgen A. Rygaard, Gentofte, Denmark

[73] Assignees: Oticon A/S, Denmark; Bernafon AG, Switzerland

[21] Appl. No.: 09/065,042
[22] PCT Filed: Oct. 31, 1995
[86] PCT No.: PCT/DK95/00430
  § 371 Date: Sep. 17, 1998
  § 102(e) Date: Sep. 17, 1998
[87] PCT Pub. No.: WO97/16122
  PCT Pub. Date: May 9, 1997
[51] Int. Cl.[6] ................................................. A61B 17/00
[52] U.S. Cl. .................... 606/151; 606/153; 606/219; 227/175.1; 227/179.1
[58] Field of Search ................................... 606/138, 151, 606/152, 153, 219; 227/175.1, 176.1, 179.1

[56] References Cited

U.S. PATENT DOCUMENTS

| | | | |
|---|---|---|---|
| 4,576,167 | 3/1986 | Noiles | 128/334 R |
| 5,119,983 | 6/1992 | Green et al. | 227/179 |
| 5,188,638 | 2/1993 | Tzakis | 606/153 |
| 5,234,447 | 8/1993 | Kaster et al. | 606/153 |
| 5,366,462 | 11/1994 | Kaster et al. | |
| 5,403,333 | 4/1995 | Kaster et al. | 606/151 |
| 5,797,934 | 8/1998 | Rygaard | 606/153 |

FOREIGN PATENT DOCUMENTS

| | | |
|---|---|---|
| 0 270 260 | 6/1988 | European Pat. Off. . |
| 0 554 990 A1 | 8/1993 | European Pat. Off. . |

*Primary Examiner*—Wynn Wood Coggins
*Assistant Examiner*—Jennifer Maynard
*Attorney, Agent, or Firm*—Larson & Taylor

[57] ABSTRACT

When performing an end-to-side anastomosis connecting the end of a first vessel to the edge region around an opening in the side wall of a second vessel, an instrument is used having a circumferential stapling anvil secured to an anvil tube accommodating the first vessel, the end of which is everted about the anvil with the intima of the end region facing the intima of the edge region, when the instrument with the first vessel in place has been inserted into the opening in the second vessel. Then, a clamping tube is advanced towards the anvil, clamping the end and edge region together against the anvil. In the next step, a number of stapling plungers carrying staples are advanced towards the anvil, the latter having staple-bending surfaces, thus stapling the two vessels together in a manner not shown. Finally, the clamping tube and the stapling plungers are withdrawn, and the whole instrument removed from the anastomosis.

12 Claims, 7 Drawing Sheets

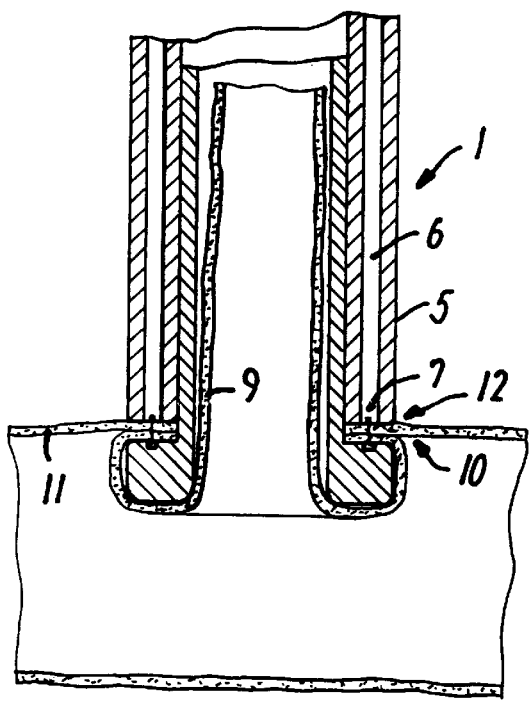
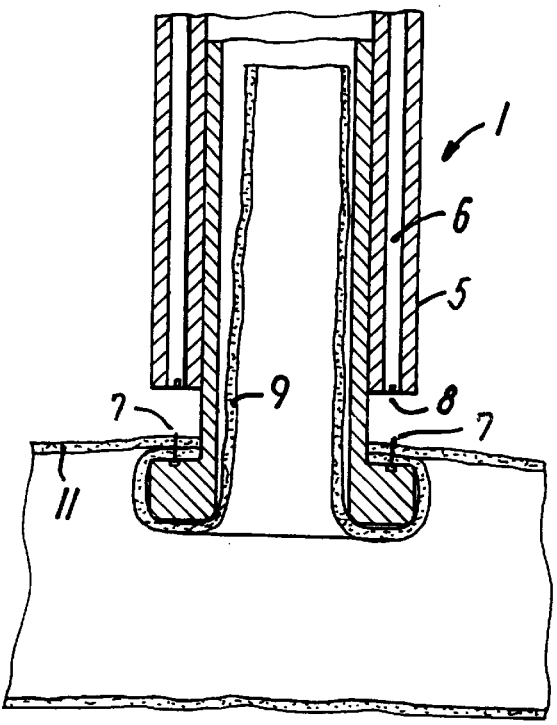
FIG.5　　　　　　　　FIG.6
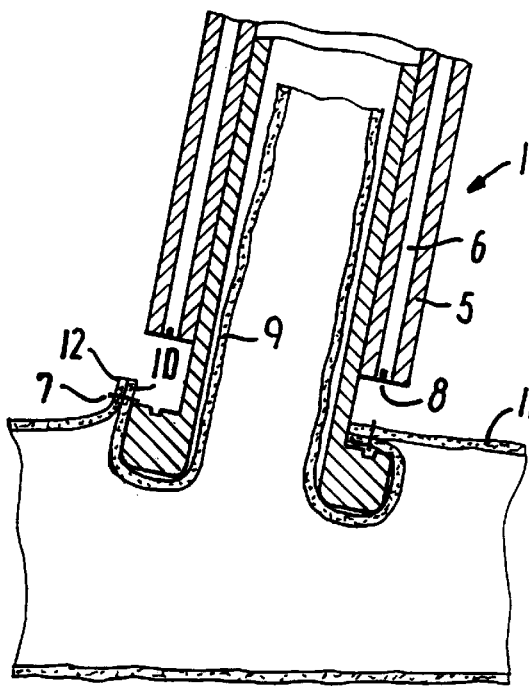
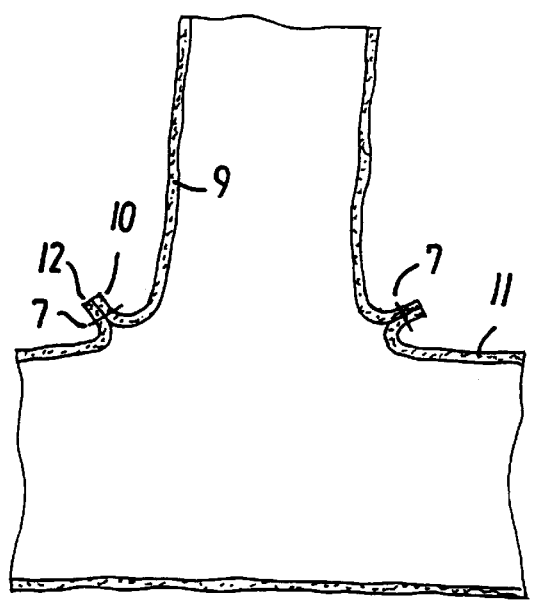
FIG.7　　　　　　　　FIG.8

METHOD AND ANASTOMOTIC INSTRUMENT FOR USE WHEN PERFORMING AN END-TO-SIDE ANASTOMOSIS

TECHNICAL FIELD

The present invention relates to a method of connecting an end region of a first vessel to the side of a second vessel by carrying out an end-to-side anastomosis, said method being of the kind comprising the following steps:

a) forming an opening in the side of said second vessel, b) inserting in said opening a generally tubular anastomosis instrument carrying said first vessel in its central longitudinal cavity and with said end region everted about a circumferential member constituting a forward portion of said instrument in such a manner that the intima side of said end region comes into contact with the intima side of said second vessel at an edge region of said opening;

c) joining said end region to said edge region by inserting penetratingly therethrough and leaving therein a plurality of spiked members; and d) removing said instrument from the joint formed between said first and second vessels.

BACKGROUND ART

A method of this kind is disclosed in the international application having the publication No. WO 95/17128. In this previously known method, the means used for interconnecting the two vessels consisted of an open springy brace carrying spikes and being capable of being bent elastically so as to make its free ends cross each other, said spikes forming angles with the brace gradually diminishing from acute angles at the free ends to substantially right angles mid-way between them. When released from the anastomotic instrument holding the brace in the elastically bent condition, it would bring the spikes into engagement with the regions to be joined so as to penetrate the latter and so to speak nail them together.

Extra-clinical trials have, however, shown that one can not always be certain that all the spikes have penetrated through the parts concerned of the two vessels to be joined, this probably being due to the limited elastic force available from the springy brace.

DISCLOSURE OF THE INVENTION

It is the object of the present invention to provide a method of the kind referred to above, with which it is possible to achieve a more reliable connection between the two vessels forming the anastomosis, and this object is achieved by utilizing in the anastomosis method an instrument which comprises i) a first elongate member, to one end of which is rigidly secured a circumferential anvil member in such a manner, said first elongate member and anvil member being hollow for acceptance of said first vessel therethrough such that said first vessel may be placed within said first elongate member with its end region everted about said anvil member with the terminal part of said end region of said first vessel facing towards the opposite end of said first elongate member, ii) staple-bending recesses provided in said anvil member and facing towards said opposite end, iii) a second elongate member longitudinally moveable relative to said first elongate member and adapted to be moved towards said anvil member so as to make it possible to clamp together therebetween said and region on said first vessel and an edge region on said second vessel, and iv) stapling plungers longitudinally moveable relative to said first and second elongate members and adapted to insert staples penetratingly through said end and edge regions into engagement with said stapling-bending recesses when said end and edge regions are clamped between said second elongate member and said anvil, so as to bend permanently said staples into a shape in which they hold said end and edge regions together. With this arrangement, the parts concerned of the two vessels to be joined are connected to each other through a stapling operation based on the same principles as other surgical stapling devices and—incidentally—ordinary office staplers.

As already indicated above, the use of stapling devices in surgical work is not unknown, but until now only in situations, in which it is possible to move the organ or organs to be operated upon from their normal position in the patient's body, such as in the abdominal cavity, to a position—not infrequently outside the patient's body—in which the anvil member, against which the staples are bent (corresponding to the lower part of an office stapler), can be placed on the side of the joint concerned facing away from the stapling plungers (corresponding to the plunger in the top part of an office stapler). Thus, the present invention is the first to offer what could be called "in-situ stapling". To make this possible, the present invention prescribes the use of an anastomosis instrument capable of performing the following four functions:

a guiding function, i.e. guiding the instrument carrying the first vessel into the opening having been formed in the side of the second vessel, an arranging function, i.e. urging the edge of the opening to the second vessel into a shape and position corresponding to the shape and position of the end region of the first vessel preparatory to a stapling function, in which the parts of the two vessels having been brought into contact through the arranging function are positively joined by a stapling operation, and a removal function, in which the instrument after completion of the stapling operation is removed from the joint formed by being luxated out of the pocket formed on the everted end of the first vessel, said pocket then unfolding simultaneously with a slight withdrawal of the first vessel.

At this point it should be emphasized that, using a preferred embodiment of the instrument, in which there is a rigid mechanical connection between the anvil member and the part of the instrument adapted to be gripped manually by the operating surgeon, both the guiding function and the arranging function referred to above may be carried out with the best possible "feel", as the surgeon will be able to sense manually any objects encountered by the anvil member, including—of course—the second vessel and the anastomotic opening formed therein.

All the functions described above may be carried out without removing the organs concerned through any significant distance away from their normal functional position in the body, making the method according to the invention eminently suitable for coronary by-pass operations. Thus, the expression "in-situ stapling" would appear justified.

The present invention also relates to an anastomotic instrument for carrying out the method according to the invention, and this instrument is characterized by the features set forth above.

Advantageous embodiments of the anastomotic instrument according to the invention, the effects of which— beyond what is self-evident—are explained in the following detailed part of the present description, are set forth in claims 3–12.

A method is disclosed in EP-A-554,990, FIG. 8, where an end-to-side anastomosis 14–15' is performed.

FIG. 8 of this document shows an end-14-to-side-15' anastomosis, but here suture 21 is used instead of clamping by moving parts, and a separate instrument 32 is used for the stapling action, i.e. not parts moving longitudinally in or around anvil 10.

Thus, it will be evident that the method and apparatus as described in EP-A-554,990 do not anticipate the method and apparatus of the present invention.

BRIEF DESCRIPTION OF THE DRAWINGS

In the following detailed part of the present description, the invention will be explained in more detail with reference to the exemplary embodiments of an anastomotic instrument according to the invention shown in the drawings, in which FIGS. 1–8 show the process of performing an end-to-side anastomosis using an anastomotic instrument according to the invention, in FIGS. 1–7 being drawn in a highly simplified manner for ease of understanding, FIGS. 9–12 in perspective and with certain parts cut away show a practical embodiment of an anastomotic instrument with the various possible relative positions of the relatively movable parts, and FIG. 13 at a highly enlarged scale shows a part of the instrument shown in FIG. 1 with modified clamping surfaces.

DESCRIPTION OF THE PREFERRED EMBODIMENTS

As mentioned above, the embodiment shown in FIGS. 1–8 of the anastomosis instrument according to the present invention constitutes a simplified version with the primary purpose of explaining the invention; this does not, however, preclude the possibility of using this embodiment in actual practice.

Figure 1:
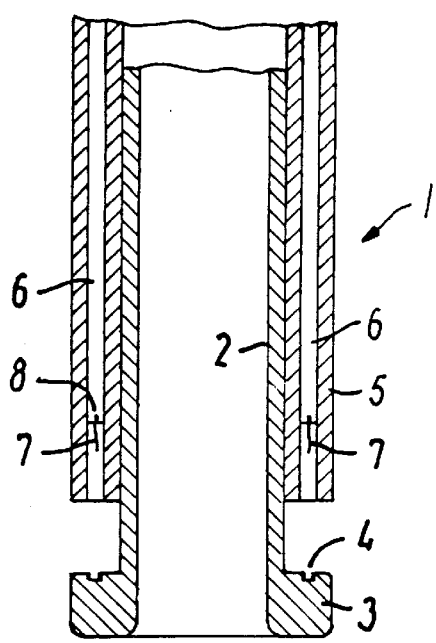

Thus, FIG. 1 shows an anastomosis instrument 1 consisting of three main components that are movable relative to each other in the longitudinal direction, i.e. in the direction shown as the vertical direction in FIG. 1:

an anvil tube 2, a clamping tube 5, and a set of stapling plungers 6.

On its lower end, the anvil tube 2 carries an anvil 3, the upper side of which is provided with a number of staple-bending recesses 4 adapted to cooperate with and bend an equal number of staples 7, in the situation shown in FIG. 1 being temporarily held lightly in an equal number of staple-holding recesses 8 formed in the lower ends of the stapling plungers 6.

Figure 2:
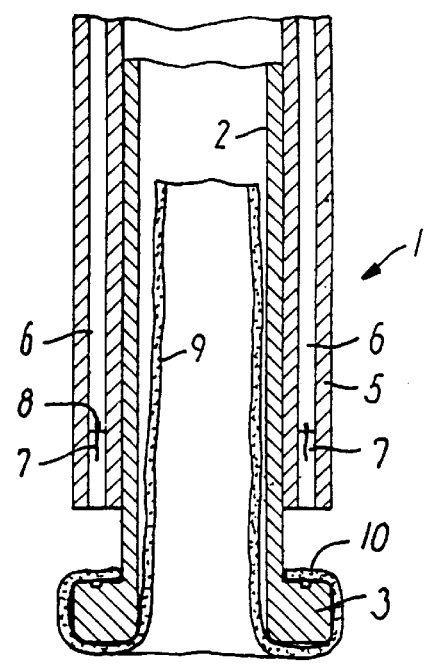

FIG. 2 shows the situation, in which the instrument is made ready for use by the operating surgeon. As mentioned initially, the anastomosis instrument according to the present invention is primarily developed for use when performing coronary bypass operations, and to this end, a bypass vessel 9—that may be a vein taken from some other part of the patient's body—has been inserted in the anvil tube with its lower end everted about the anvil 3 and with its end region 10 covering the staple-bending recesses 4 in the upper surface of the anvil 3. At this point it should be noted that the bypass vessel 9 may have a considerably larger circumference than the inside of the anvil tube 2, consequently lying more or less folded in the longitudinal direction in the latter, for which reason the action of everting its end region 10 about the anvil 3 does not necessarily entail undue stretching of the bypass vessel 9.

Figure 3:
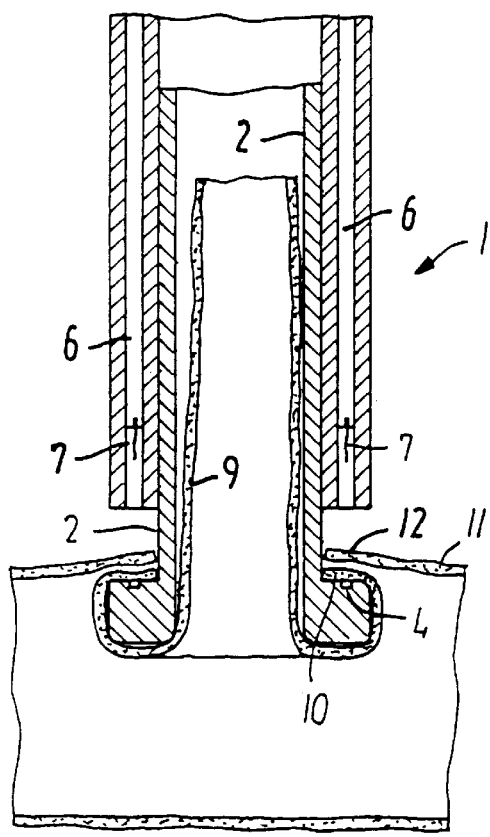

FIG. 3 shows the instrument having been made ready as shown in FIG. 2 inserted in an opening in a coronary artery 11, said opening having an edge region 12 which, due to the elasticity of the tissue of the coronary artery 11, will embrace the anvil tube 2 in a location close to the anvil 3. The opening in the coronary artery 11 may e.g. have been formed according to the method described in the international application with publication No. WO 95/17127 with the title "Method and instrument for establishing the receiving side of a coronary artery bypass graft".

Figure 4:
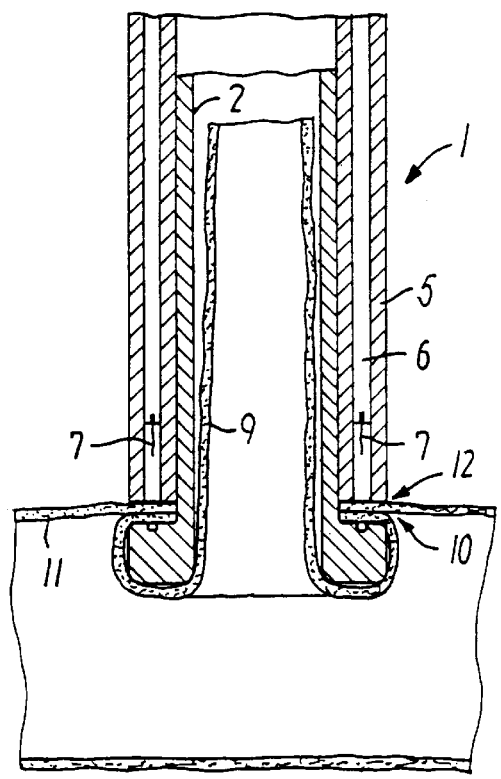

As soon as the operating surgeon in the situation shown in FIG. 3 has ascertained that the edge region 12 embraces the anvil tube 2 closely on all sides, he or she will proceed to the situation shown in FIG. 4, in which the clamping tube 5 has been moved towards the anvil 3 so as to clamp the edge region 12 on the coronary artery 11 and the end region 10 on the bypass vessel 9 firmly together in readiness for the next step shown in FIG. 5, in which the stapling plungers 6 have been moved downwardly so as to cause the staples 7 to penetrate the edge region 12 and the end region 10 and engage the staple-bending recesses 4, by which they will be bent in a tangential direction in a similar manner as is known from both surgical staplers and ordinary office staplers.

In the situation shown in FIG. 6, the clamping tube 5 together with the stapling plungers 6 have been moved outwardly and away from the staples 7, the staple-holding recesses 8 due to their light holding action having let go of the staples 7, the latter also having been anchored in the end region 10 by their bent ends.

FIG. 7 shows the situation, in which the operation of removing the anastomosis instrument 1 from the coronary artery 11 and its anastomosis with the bypass vessel 9 has begun. As will be seen from FIGS. 6 and 7, the circumferential pocket formed by the eversion of the lower end of the bypass vessel 9 will now open and allow the anvil 3 to be removed by luxation, FIG. 8 showing the situation after such removal, resulting in a finished anastomosis of the intima-to-intima type considered most desirable for this type of operation.

The three main components of the anastomosis instrument 1 referred to above, i.e. the anvil tube 2, the clamping tube 5 and the set of stapling plungers 6, will, of course, have to be connected to some kind of operating members to enable the operating surgeon and his or her assistants to carry out the steps shown in FIGS. 1–8. Theoretically, these operating members could consist of three tubes (not shown), viz.

a relatively long holding tube in continuation of the anvil tube 2, a somewhat shorter clamping tube in continuation of the clamping tube 5, and an even shorter stapling tube, to which the stapling plungers 6 are connected.

As is well-known, however, coronary bypass operations, especially according to the method of the international application referred to above, should be carried out as rapidly as possible, and for this reason, the "theoretical" embodiment shown in FIGS. 1–7 is too cumbersome to work with to ensure a sufficiently rapid operating procedure. As mentioned above, FIGS. 9–12 illustrate an embodiment of an anastomosis instrument according to the present invention, that is highly suitable for creating an end-to-side anastomosis in a very short time.

Due to the construction of the instrument shown in FIGS. 9–12 it is not possible to make an easily understandable drawing in the nature of the simple drawings of FIGS. 1–7. For this reason, the "active" parts of the instrument have been shown in perspective, and with the exception of the anvil and its supporting columns, with one half removed along a longitudinal sectional plane, so that the remaining half can be seen partly from the inside, partly from the outside. In FIGS. 9–12, those of the components functionally corresponding to components shown in FIGS. 1–7 have been given the same reference numbers with 100 added, whereas components not having "opposite numbers" in FIGS. 1–7 have been given the reference numbers of the components, with which they are most closely associated, with the addition of a capital letter.

Figure 9:
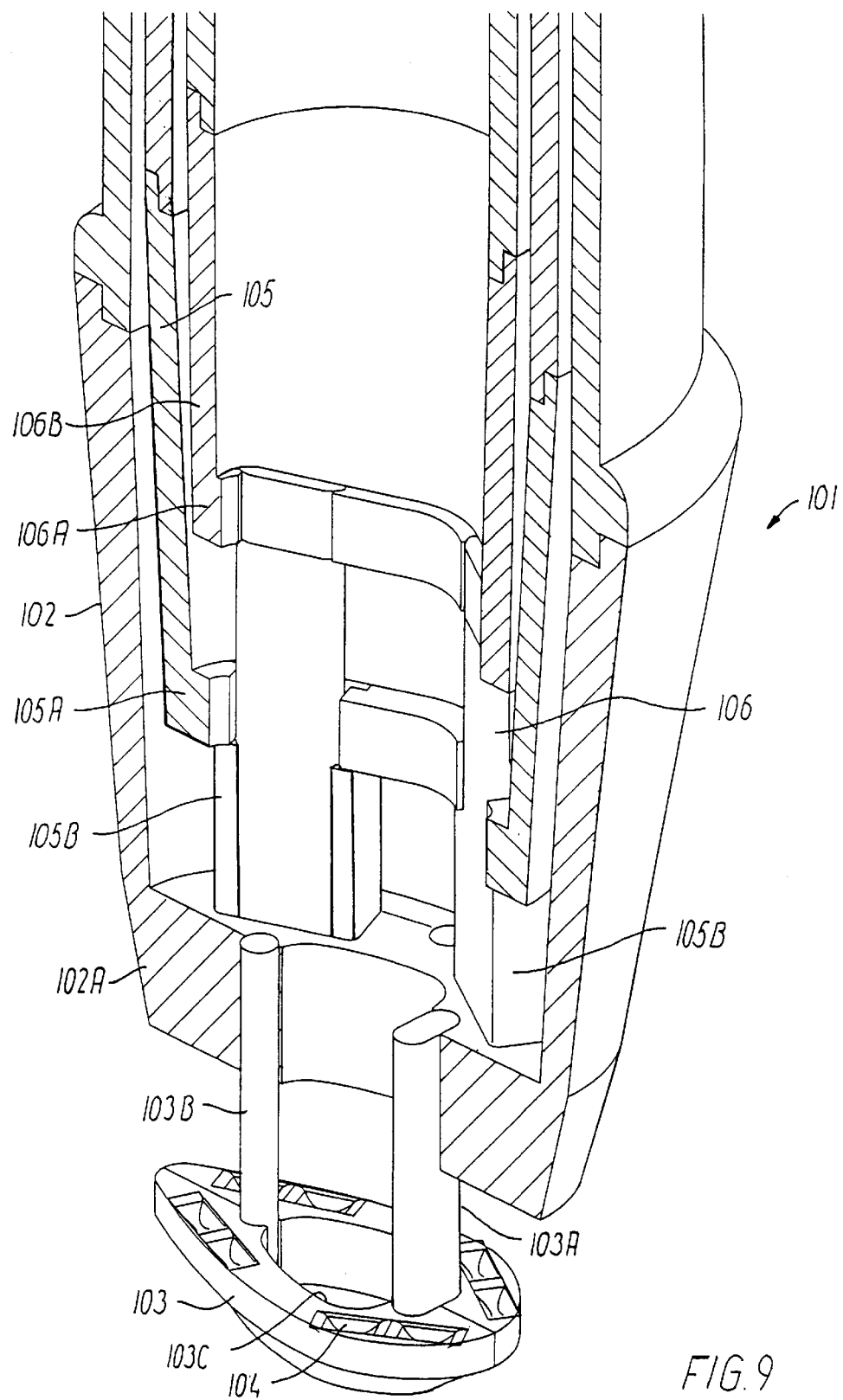

As shown in FIG. 9, the anastomosis instrument 101 comprises a number of parts functionally corresponding to parts of the instrument shown in FIGS. 1–7, viz.:
 an anvil tube 102,
 an anvil 103,
 a clamping tube 105, and
 a set of stapling plungers 106.

Although the basic functions of these parts are the same as the basic functions of the corresponding parts in the embodiment of FIGS. 1–7, the arrangement differs somewhat from that of the latter, as will be evident from the following.

In contrast to the anvil tube 2 of FIG. 1, the anvil tube 102 of FIG. 9 extends on the outside of the instrument and is terminated by an end wall 102A, to which the anvil 103 is secured at a distance by means of two columns, viz. an upstream column 103A and a downstream column 103B. The expressions "upstream" and "downstream" refer to the direction of blood flow in the artery, in which the instrument 101 is intended to be used in creating an end-to-side anastomosis.

To make it possible to insert the bypass vessel (not shown) corresponding to the bypass vessel 9 shown in FIGS. 1–8, all transversely oriented components have suitable openings, of which the forwardmost opening 103C is formed in the anvil 103, the latter being provided with staple-bending recesses 104 having the same function as the staple-bending recesses 4 shown in FIG. 1.

As will be seen from FIGS. 9–12, the various components are not rotationally symmetrical about the longitudinal axis of the instrument, as the anvil 103 has been made "boat-shaped" to make it easier to insert it in the opening in the artery and to make it easier for the edges of the opening to fit in with the upper side of the anvil 103 with the stapling recesses 104.

Due to the arrangement of the anvil tube 102 as the outermost component terminated by the end wall 102A, it is not possible in this embodiment to let the clamping tube 105 extend in its full circumferential width all the way towards the upper face of the anvil 103. For this reason, the clamping tube 105 is terminated by an end wall 105A, from which a set of clamping columns 105B extend in the forward (downward) direction through suitable openings in the anvil tube end wall 102A.

The stapling plungers 106 are guided in the longitudinal direction in suitable guides in the clamping columns 105B, and their rearmost (uppermost) ends are secured to a stapling plunger carrier 106A, itself secured to and terminating a stapling tube 106B, through which the force for actuating the stapling plungers 106 may be transmitted from a suitable operating device. FIGS. 9–12 show neither staples corresponding to the staples 7 of FIG. 1 nor staple-holding recesses corresponding to the staple-holding recesses 8 shown in FIG. 1, but it will be understood that the forwardmost (lowermost) ends of the stapling plungers 106 will be provided with suitable staple-holding recesses capable of holding staples in such a position, that when the stapling plungers 106 are advanced towards the anvil 103, the staples will be bent by the staple-bending recesses 104 in the usual manner.

The relative positions of the various parts as shown in FIG. 9 correspond to those shown in FIGS. 1–3, i.e. there is a sufficient distance between the rearward (upper) face of the anvil 103 and the forward (downward) ends of the clamping columns 105B to accomodate the everted end region of the bypass vessel corresponding to the end region 10 shown in FIG. 2, as well as the edge region of the coronary artery concerned corresponding to the edge region 12 of the coronary artery 11 shown in FIG. 3.

Figure 10:
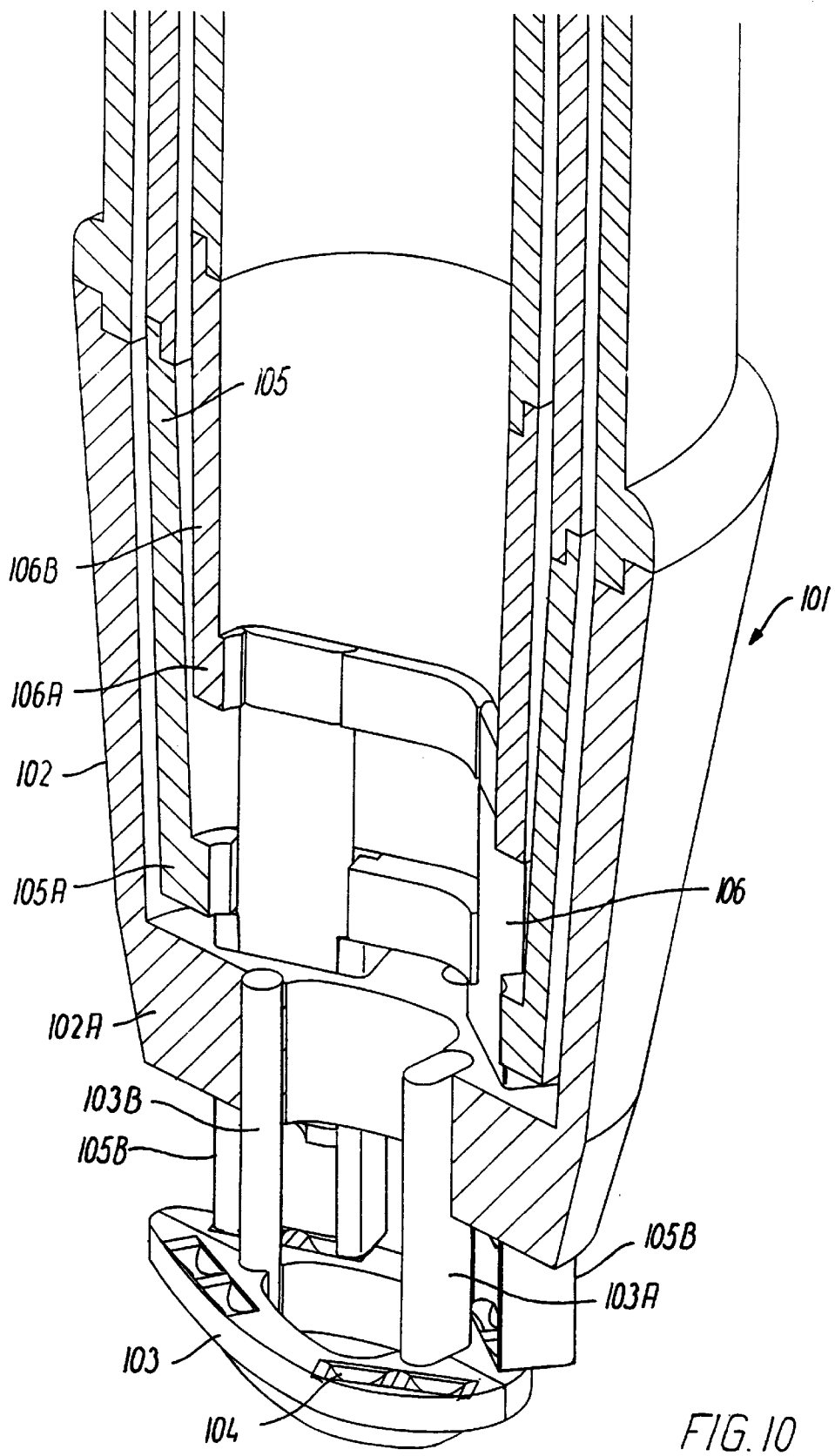

The situation shown in FIG. 10 corresponds to that shown in FIG. 4, i.e. the clamping columns 105B have been advanced towards the anvil 103, in FIG. 10 leaving a gap symbolizing the presence of the end region of the bypass vessel and the edge region of the coronary artery (all not shown). The movement of the clamping columns 105B has, of course, been effected by advancing the clamping tube 105 to the same extent. To prevent said end and edge regions being crushed in the clamping operation, suitable stops (not shown) are adapted to stop the movement of the clamping columns 105B towards the anvil 103 so as to leave a gap just sufficient to hold them firmly together. To improve the grip, the clamping surfaces may be provided with elastically flexible fins or fingers 13 as shown in FIG. 13. This Figure shows how this concept could be applied to the embodiment shown in FIGS. 1–7, it being—of course—equally applicable to that shown in FIGS. 9–12.

Figure 11:
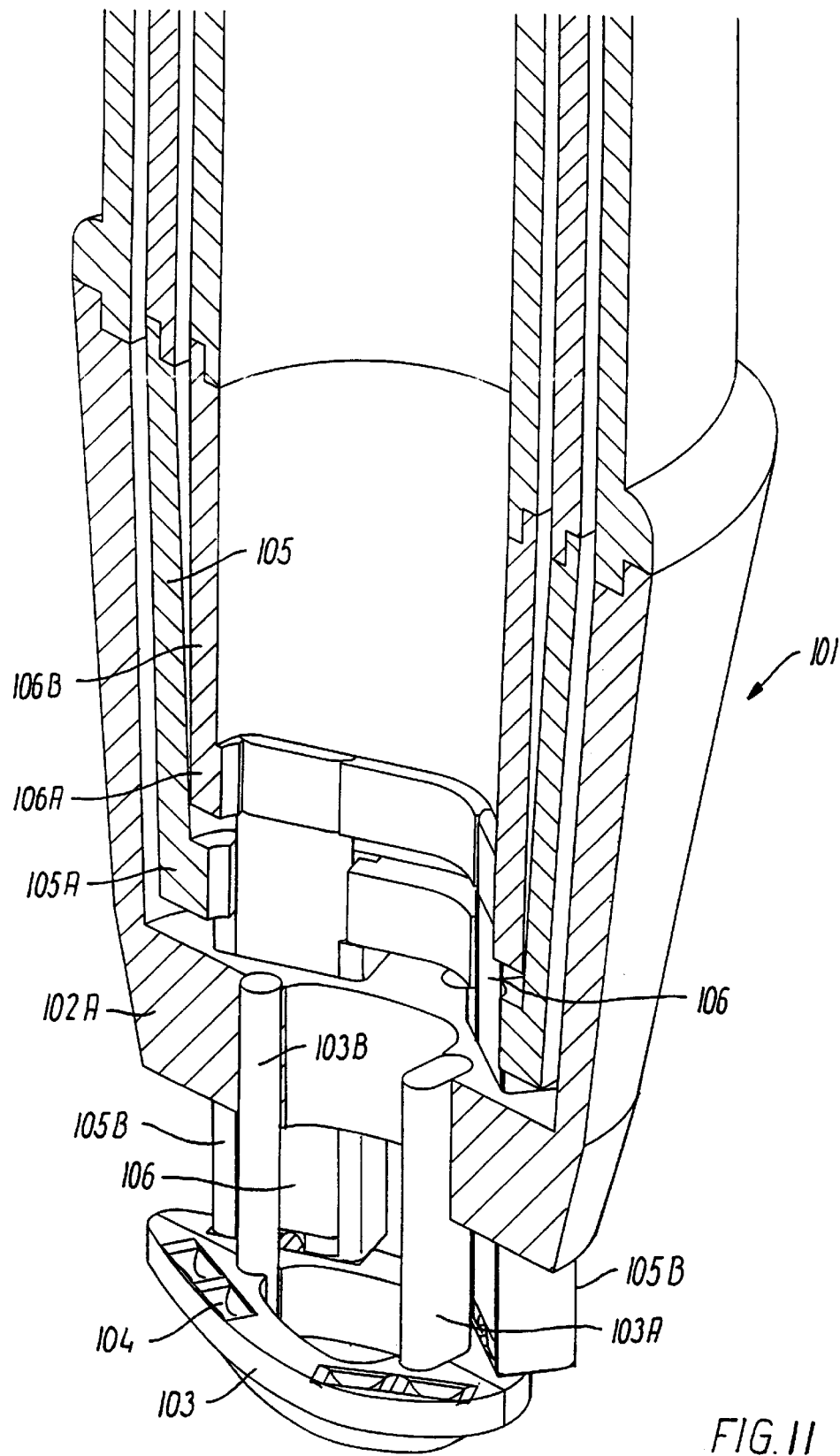

The relative positions shown in FIG. 11 correspond to those shown in FIG. 5, i.e. the stapling plungers 106 have now been advanced, guided by the clamping columns 105B so as to bring the staples (not shown) into engagement with the staple-bending recesses 104, thus joining the end region of the bypass vessel to the edge region of the coronary artery (all not shown).

Figure 12:
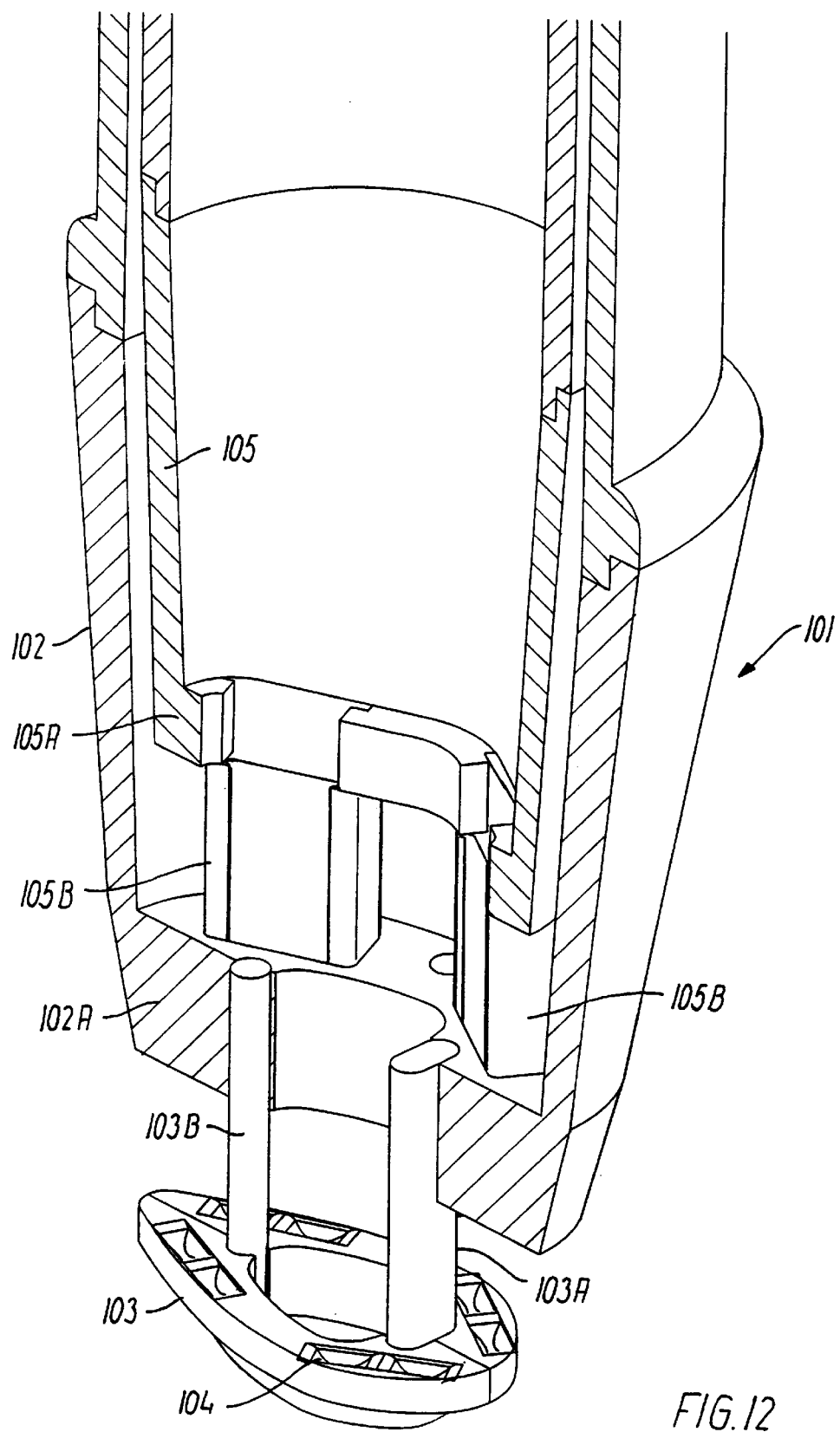
Figure 13:
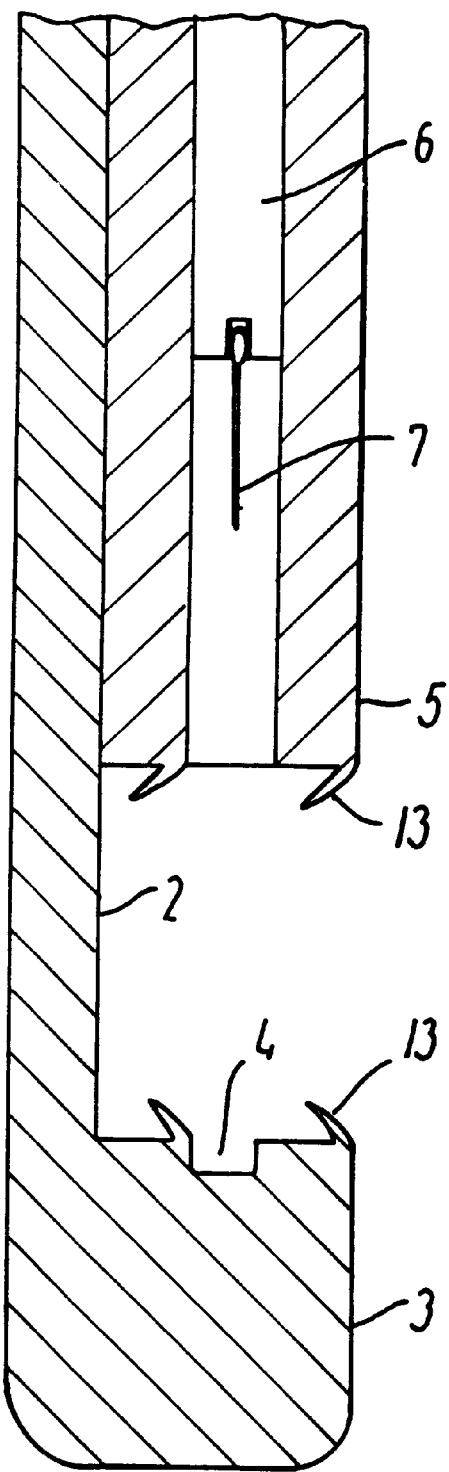

The relative positions shown in FIG. 12 correspond to those shown in FIGS. 6 and 7 and with the exception that in FIG. 12, the stapling plungers 106 have not only been withdrawn from the staples joining the two vessels, but have in fact been removed completely from the instrument to make it possible to insert a new set of staples, that may be of the disposable or semi-disposable type.

With the arrangement shown in FIGS. 9–12, the operating surgeon may literally have a firm grip on the situation by holding the outermost component, i.e. the anvil tube 102, which is rigidly connected to the anvil 103 through the columns 103A and 103B, so that he or she will be able to move the anvil 103 with the everted end of the bypass vessel into the opening in the coronary artery by direct manual control, and—not least—by "direct mechanical feedback", as the rigid mechanical interconnection between the anvil 103 and the anvil tube 102 enables the surgeon to "feel" whatever object is encountered by the anvil. Advantageously, the rearward (upper) part (not shown) of the instrument may comprise suitable operating devices and/or mechanisms for moving the clamping tube 105 and the stapling plungers 106 relatively to the anvil tube 102 and hence relatively to the anvil 103. Due to the extremely limited time available for performing coronary bypass operations, these operating devices and/or mechanisms should be designed to enable the operating surgeon to initiate the requisite movements rapidly and with a minimum of effort.

Thus, the operating devices and/or mechanisms could be arranged to function under the control of a single operating member, such as a push-button on the rear (upper) end of the instrument adapted to be operated by the surgeon's thumb, in the following manner:

firstly, when the operating member is moved in a first direction, e.g. a push-button is depressed, the clamping columns 105B will be advanced to their forwardmost (lower) position, in which they clamp the end region of the bypass vessel and the edge region of the opening in the artery together until said stop is reached, and then the stapling plungers 106 will immediately be actuated to staple the two regions together, after which both the clamping columns 105B and the stapling plungers 106 are withdrawn, e.g. by releasing said push-button, and secondly, immediately upon the operating member moving in the opposite direction, e.g. when the push-button has been released, the mechanism is re-set in readiness for a movement in the first direction, after which the instrument can be removed as described above with reference to FIG. 7.

It should be possible for a technician skilled in the art of designing and making surgical instruments comprising operating mechanisms to design and construct an operating device or mechanism capable of operating in the manner described above, for which reason these parts have not been described or shown in detail.

LIST OF PARTS

1 anastomosis instrument
2 anvil tube
3 anvil
4 staple-bending recess
5 clamping tube
6 stapling plunger
7 staple
8 staple-holding recess
9 bypass vessel
10 end region
11 coronary artery
12 edge region
13 fin or finger
101 anastomosis instrument
102 anvil tube
102A (anvil tube) end wall
103 anvil
103A (anvil) upstream column
103B (anvil) downstream column
103C (anvil) opening
104 staple-bending recess
105 clamping tube
105A (clamping tube) end wall
105B clamping column (and stapling-plunger guide)
106 stapling plunger
106A stapling plunger carrier
106B stapling tube

I claim:

1. In a method of connecting an end region of a first vessel to the side of a second vessel by carrying out an end-to-side anastomosis, said method comprising the following steps a–d:

a) forming an opening in the side of said second vessel, b) inserting in said opening a generally tubular anastomosis instrument carrying said first vessel in its central longitudinal cavity and with said end region everted about a circumferential member constituting a forward portion of said instrument in such a manner that the intima side of said end region comes into contact with the intima side of said second vessel at an edge region of said opening, c) joining said end region to said edge region by inserting penetratingly therethrough and leaving therein a plurality of spiked members, and d) removing said instrument from the joint formed between said first and second vessels, the improvement which comprises using in said method an anastomosis instrument which comprises i) a first elongate member, to one end of which is rigidly secured a circumferential anvil member, said first elongate member and anvil member being hollow for acceptance of said first vessel therethrough such that said first vessel may be placed within said first elongate member with its end region everted about said anvil member with the terminal part of said end region of said first vessel facing towards the opposite end of said first elongate member, ii) staple-bending recesses provided in said anvil member and facing towards said opposite end, iii) a second elongate member longitudinally moveable relative to said first elongate member and adapted to be moved towards said anvil member so as to make it possible to clamp together therebetween said end region on said first vessel and an edge region on said second vessel, and iv) stapling plungers longitudinally moveable relative to said first and second elongate members and adapted to insert staples penetratingly through said end and edge regions into engagement with said stapling-bending recesses when said end and edge regions are clamped between said second elongate member and said anvil, so as to bend permanently said staples into a shape in which they hold said end and edge regions together.

2. Anastomotic instrument for carrying out the method of claim 1, comprising a) a first elongate member to one end of which is rigidly secured a circumferential anvil member, said first elongate member and anvil member being hollow for acceptance of said first vessel therethrough such that said first vessel may be placed within said first elongate member with its end region everted about said anvil member with the terminal part of said end region of said first vessel facing towards the opposite end of said first elongate member, b) staple-bending recesses provided in said anvil member and facing towards said opposite end, c) a second elongate member longitudinally moveable relative to said first elongate member and adapted to be moved towards said anvil member so as to make it possible to clamp together therebetween said end region on said first vessel and an edge region on said second vessel, and d) stapling plungers longitudinally moveable relative to said first and second elongate members and adapted to insert staples penetratingly through said end and edge regions into engagement with said stapling-bending recesses when said end and edge regions are clamped between said second elongate member and said anvil, so as to bend permanently said staples into a shape in which they hold said end and edge regions together.

3. Anastomotic instrument according to claim 2, wherein the external surface of said first elongate member constitutes at least a part of the external surface of said instrument, so as to make it possible to hold the latter by manually gripping the former.

4. Anastomotic instrument according to claim 3, wherein said first elongate member is rigidly connected to said anvil member through an end wall rigidly secured to or integral with an end of said first elongate member and at least one connecting member rigidly secured to said end wall and said anvil member.

5. Anastomotic instrument according to claim 4, wherein said second elongate member comprises
 a) a rearward part longitudinally moveable in said first elongate member,
 b) an intermediate part rigidly secured to or integral with said rearward part and
 c) a plurality of forward clamping columns, each at its rear end being rigidly secured to said intermediate part, each extending through said end wall, and each at its forward end having a clamping surface facing said anvil member.

6. Anastomotic instrument according to claim 5, wherein each stapling plunger is rigidly secured to a stapling plunger carrier rigidly secured to a third elongate member longitudinally moveable in said rearward part of said second elongate member, each stapling plunger extending moveably through said intermediate part and said clamping columns.

7. Anastomotic instrument according to claim 2, further comprising a stop member which limits movement of said second elongate member such that said second elongate member can only be advanced relative to said first elongate member and said anvil member to a limiting position leaving a gap between said second elongate member and said anvil, said gap being slightly smaller than the combined thickness of an end region and an edge region of vessels to be connected.

8. Anastomotic instrument according to claim 7, further comprising a mechanism adapted to move said second elongate member and said stapling plungers relative to said first elongate member and said anvil member in dependence on the movement of a single operating member moveable in a first direction and then returnable in the opposite direction in the following manner:
 a) when said operating member is moved in said first direction, said second elongate member is advanced to said limiting position immediately upon which said stapling plungers are actuated to join said end region to said edge region, immediately upon which both said second elongate member and said stapling plungers are withdrawn to leave a large gap between said clamping columns and said anvil member said large gap being sufficiently large to allow the instrument to be removed from the joint, and when said operating member is moved in said second direction, the mechanism is re-set in readiness for a new movement in said first direction.

9. Anastomotic instrument according to claim 8, further comprising means adapted to move said operating member in said second direction as soon as the force moving it in said first direction is removed.

10. Anastomotic instrument according to claim 2, wherein said second elongate member and said anvil have mutually cooperating clamping surfaces, and wherein at least one of said clamping surfaces has a gripping effect on tissue parts clamped between said clamping surfaces.

11. Anastomotic instrument according to claim 10, wherein said gripping effect comprises surface roughening or embossing.

12. Anastomotic instrument according to claim 10, wherein said gripping effect comprises elastically flexible fins or fingers which in a relaxed state extend obliquely inwardly.

* * * * *